(12) United States Patent
Ghagare et al.

(10) Patent No.: US 9,993,561 B2
(45) Date of Patent: *Jun. 12, 2018

(54) RIFAXIMIN COMPLEXES

(71) Applicant: Cipla Limited, Mumbai (IN)

(72) Inventors: Maruti Ganpati Ghagare, Mumbai (IN); Sunilkumar Parasnath Saroj, Mumbai (IN); Dharmaraj Ramachandra Rao, Mumbai (IN); Rajendra Narayanrao Kankan, Mumbai (IN)

(73) Assignee: CIPLA Limited, Mumbai (IN)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/521,292

(22) Filed: Oct. 22, 2014

(65) Prior Publication Data

US 2015/0045382 A1   Feb. 12, 2015

Related U.S. Application Data

(63) Continuation of application No. 13/132,054, filed as application No. PCT/GB2009/002854 on Dec. 9, 2009, now Pat. No. 8,916,193.

(30) Foreign Application Priority Data

Dec. 10, 2008 (IN) .......................... 2577/MUM/2008

(51) Int. Cl.
| | |
|---|---|
| A61K 47/48 | (2006.01) |
| A61K 47/40 | (2006.01) |
| A61K 9/20 | (2006.01) |
| A61K 31/4184 | (2006.01) |
| A61K 31/437 | (2006.01) |
| A61K 47/32 | (2006.01) |
| B82Y 5/00 | (2011.01) |
| A61K 47/58 | (2017.01) |
| A61K 47/69 | (2017.01) |

(52) U.S. Cl.
CPC ............ *A61K 47/40* (2013.01); *A61K 9/2095* (2013.01); *A61K 31/4184* (2013.01); *A61K 31/437* (2013.01); *A61K 47/32* (2013.01); *A61K 47/58* (2017.08); *A61K 47/6951* (2017.08); *B82Y 5/00* (2013.01)

(58) Field of Classification Search
None
See application file for complete search history.

(56) References Cited

U.S. PATENT DOCUMENTS

| | | | |
|---|---|---|---|
| 8,916,193 B2 * | 12/2014 | Ghagare et al. .............. | 424/464 |
| 2009/0312357 A1 * | 12/2009 | Rao et al. .................... | 514/279 |

FOREIGN PATENT DOCUMENTS

| | | |
|---|---|---|
| JP | 2007/516291 A | 6/2007 |
| JP | 5756020 A | 6/2015 |

(Continued)

*Primary Examiner* — Robert A Wax
*Assistant Examiner* — Melissa S Mercier
(74) *Attorney, Agent, or Firm* — Toan P. Vo; Bass Berry & Sims PLC

(57) ABSTRACT

There is provided a complex comprising rifaximin and a complexing agent, wherein the complexing agent is a polyvinyl pyrrolidone (PVP) or a cyclodextrin. There is also provided a process for preparing the complex, a pharmaceutical composition including the complex and therapeutic uses of the complex.

22 Claims, 10 Drawing Sheets

(56) References Cited

FOREIGN PATENT DOCUMENTS

Figure 1:
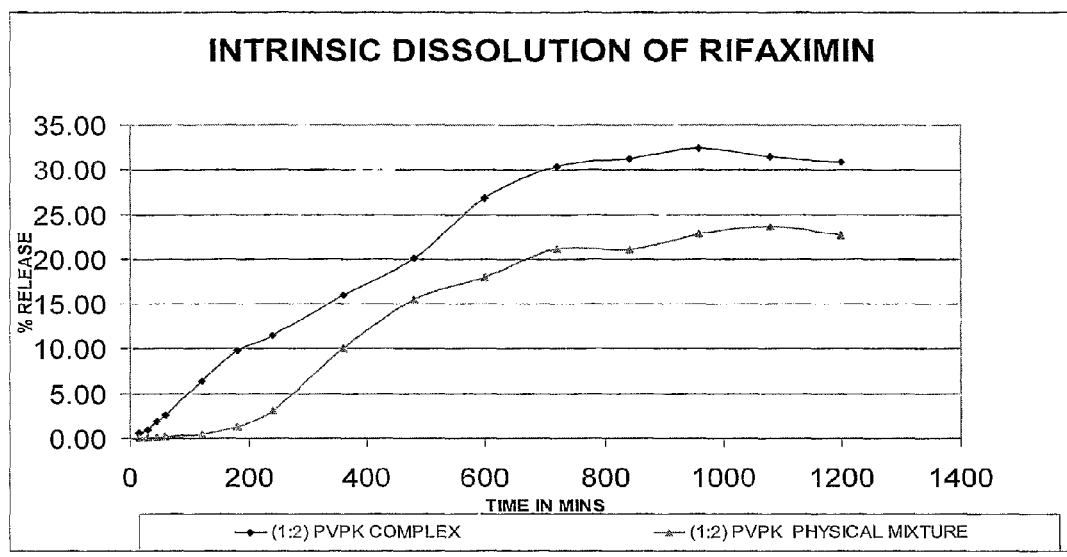

| WO | WO9904823 | * | 2/1999 |
|----|-----------|---|--------|
| WO | 2005/062882 A2 | | 7/2005 |
| WO | 2007/047253 A2 | | 4/2007 |
| WO | 2008/016708 A2 | | 2/2008 |
| WO | 2010/067072 A1 | | 6/2010 |

* cited by examiner

RIFAXIMIN COMPLEXES

CROSS REFERENCE TO RELATED APPLICATIONS

This application is a continuation of U.S. patent application Ser. No. 13/132,054 having a 371(c) date of Jul. 8, 2011, issued as U.S. Pat. No. 8,916,193, which was a filing under 35 U.S.C. 371 of International Application No. PCT/GB2009/002854, filed Dec. 9, 2009, claiming priority to Indian Patent Application No. 2577/MUM/2008, filed Dec. 10, 2008, which applications are all incorporated herein by reference in their entirety.

TECHNICAL FIELD OF THE INVENTION

The present invention relates to complexes of rifaximin and processes for preparing such complexes.

BACKGROUND

Rifaximin is a semi-synthetic, rifamycin antimicrobial drug with in vitro activity against Gram-positive, Gram-negative and anaerobic bacteria. It acts by inhibiting bacterial ribonucleic acid (RNA) synthesis. Rifaximin is chemically termed as (2S, 16Z, 18E, 20S,21S, 22R, 23R, 24R, 25S, 26S, 27S, 28E)-5,6,21,23,25-pentahydroxy-27-methoxy-2,4,11,16,20,22,24,26-octamethyl-2,7-(epoxypentadeca-[1,11,13]-trienimino)benzofuro-[4,5-e]-pyrido-[1,2-a]-benzimidazole-1,15-(2H)-dione, 25-acetate (I).

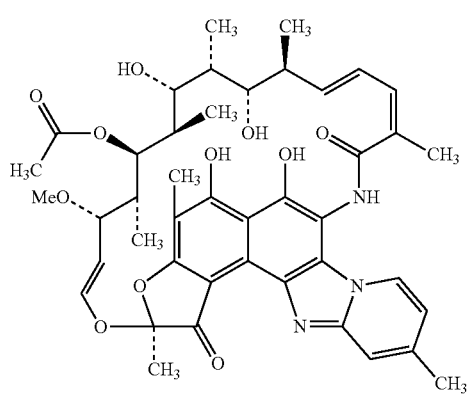

Rifaximin is used for treatment of travelers' diarrhea caused by noninvasive strains of *Escherichia coli*.

WO2009137672 discloses a method of treating bowel disease (BD), comprising administering a gastrointestinal cleanser to a subject in need thereof; and administering a therapeutically effective amount of an antibiotic.

Rifaximin was first disclosed in U.S. Pat. No. 4,341,785 which also discloses a process for its preparation and a method for crystallization of rifaximin by using suitable solvents or a mixture of solvents. This patent does not mention polymorphism of rifaximin.

U.S. Pat. No. 4,557,866, and its equivalent CA1215976, disclose processes for the preparation of rifaximin.

WO2007047253 discloses a pharmaceutical composition of hydroxybutenyl cyclodextrins with antifungal azole compounds. However, this application does not provide any enabling methods nor proof of advantages of such a complex.

WO2008035109 discloses the amorphous form of rifaximin.

U.S. Pat. No. 7,045,620, discloses various crystalline polymorphic forms of rifaximin which are termed as rifaximin α, rifaximin β and rifaximin γ. These polymorphic forms are characterized using X-ray powder diffraction. According to U.S. Pat. No. 7,045,620, the presence of water within the crystallization solvent plays an important role in crystal formation. Thus, rifaximin polymorphs undergo changes with a change in the moisture content, and interconversion of one form to another occurs with an increase or decrease in the water content.

U.S. Pat. No. 7,045,620 further discloses rifaximin α which has a water content between 2.0% and 3.0%, rifaximin β which has a water content between 5.0% and 6.0%, and rifaximin γ which is poorly crystalline and has a water content between 1.0% and 2.0%.

EP1698630 discloses further polymorphic forms of rifaximin termed as δ and ε. The stability of these forms also depends upon the water content.

However, all these forms are hygroscopic and they have a tendency to interconvert from one to another. Thus, these forms are difficult to handle as well as store and they require controlled conditions, specifically, humidity and temperature during handling and storage.

Thus, transformations of polymorphic forms of drug substances are of great disadvantage, because they cause difficulties in fulfilling pharmaceutical requirements and specifications. The physicochemical properties of products that exhibit such polymorphic change vary according to the actual ratio of polymorphic forms. This causes further difficulties while formulating the polymorphic forms into suitable dosage forms.

Also, as rifaximin is sparingly soluble in water, the formulation chemist finds it difficult to prepare a consistent formulation using the known polymorphic forms. Hence, there is a need to prepare rifaximin in a form which is suitable for formulation and has increased solubility and stability.

SUMMARY OF THE INVENTION

According to a first aspect of the present invention, there is provided a form of rifaximin with enhanced solubility and stability. This form of rifaximin is a complex comprising rifaximin and a complexing agent.

According to another aspect of the present invention, there is provided a complex comprising rifaximin and a complexing agent. Throughout this specification, this complex may be referred to as "the rifaximin complex". In an embodiment, the complex comprises solely rifaximin and the complexing agent, i.e. no other components are present in the complex.

Advantageously, the complex of the present invention exhibits enhanced solubility and stability, particularly compared to a physical mixture of rifaximin and a complexing agent.

The complexing agent used in the present invention comprises a polyvinyl pyrrolidone (PVP) or a cyclodextrin (CD).

In an embodiment, the complexing agent is a PVP. In an alternative embodiment, the complexing agent is a CD.

In an embodiment, the complexing agent is not hydroxybutenyl cyclodextrin or sulfonyl hydroxybutenyl cyclodextrin.

In an embodiment, the complexing agent is a PVP having a K-value ranging from K-15 to K-90. Suitably, the complexing agent is a PVP selected from the group consisting of PVP K-12, K-15, K-17, K-25, K-30, K-60, K-80, K-90 and K-120, preferably, K-25, K-30 or K-90. Typically, the complexing agent is PVP K-30.

In an embodiment, the complexing agent is an unmodified cyclodextrin. In other words, the CD is a cyclic glucose oligosaccharide in which none of the hydroxyl groups has been modified. In an embodiment, the complexing agent is a cyclodextrin selected from the group consisting of α-cyclodextrin, β-cyclodextrin or γ-cyclodextrin, preferably β-cyclodextrin.

In an embodiment, the weight ratio of rifaximin to complexing agent ranges from 20:1 w/w to 1:20 w/w. It is to be understood that "w/w" means by weight. Advantageously, the ratio of rifaximin to complexing agent ranges from 10:1 w/w to 1:2 w/w. Typically, the ratio of rifaximin to complexing agent ranges from 4:1 w/w to 1:2 w/w. The ratio may be 1:1 w/w.

According to another aspect of the present invention, there is provided the rifaximin complex characterized by having an intrinsic dissolution profile as shown in any one of FIGS. 1 to 8.

According to another aspect of the present invention, there is provided a process for preparing a complex comprising rifaximin and a complexing agent, the process comprising:
a) dissolving rifaximin in a solvent;
b) adding the complexing agent to the rifaximin solution to form a mixture;
c) isolating the complex from the reaction mass obtained in step b).

In an embodiment, the complex comprises solely rifaximin and the complexing agent, i.e. no other components are present in the complex.

The complexing agent used in the process comprises a polyvinyl pyrrolidone (PVP) or a cyclodextrin (CD).

In an embodiment, the complexing agent is a PVP. In an alternative embodiment, the complexing agent is a CD.

In an embodiment, the complexing agent is a PVP having a K-value ranging from K-15 to K-90. Suitably, the complexing agent is a PVP selected from the group consisting of PVP K-12, K-15, K-17, K-25, K-30, K-60, K-80, K-90 and K-120, preferably, K-25, K-30 or K-90. Typically, the complexing agent is PVP K-30.

In an embodiment, the complexing agent is a cyclodextrin selected from the group consisting of α-cyclodextrin, β-cyclodextrin or γ-cyclodextrin, preferably β-cyclodextrin.

In an embodiment, the weight ratio of rifaximin to complexing ranges from 20:1 w/w to 1:20 w/w. It is to be understood that "w/w" means by weight. Advantageously, the ratio of rifaximin to complexing agent ranges from 10:1 w/w to 1:2 w/w. Typically, the ratio of rifaximin to complexing agent ranges from 4:1 w/w to 1:2 w/w. The ratio may be 1:1 w/w. Thus, according to another aspect of the present invention, there is provided a complex comprising rifaximin and a complexing agent, wherein the weight ratio of rifaximin to complexing ranges from 20:1 w/w to 1:20 w/w, preferably from 10:1 w/w to 1:2 and more preferably from 4:1 w/w to 1:2 w/w.

The rifaximin used in the process of the present invention may be in any polymorphic form or in a mixture of any polymorphic forms.

The complexing agent may be added to the rifaximin solution as such or in the form of a solution with a solvent.

The solvent for the rifaximin may be selected from the group consisting of an ether, an alcohol, an ester, an aldehyde, a halogenated solvent, a hydrocarbon and mixtures thereof. Preferably, the solvent is an alcohol, for example methanol or ethanol. Typically, the solvent is ethanol.

The complexing agent may be added to the rifaximin in the form of a solution. In which case, the solvent for the complexing agent may be selected from the group consisting of an ether, an alcohol, an ester, an aldehyde, a halogenated solvent, a hydrocarbon and mixtures thereof. Preferably, the solvent is an alcohol, for example methanol or ethanol. Typically, the solvent is ethanol.

Alternatively, the complexing agent may be added to the rifaximin solution as such, i.e. not in the form of a solution.

Suitably, the isolation comprises concentrating the reaction mass obtained in step b), and drying to obtain the isolated complex.

According to another aspect of the present invention, there is provided a complex prepared according to the process described above.

According to another aspect of the present invention, there is provided a complex comprising rifaximin and a complexing agent, which complex enhances at least one of the following:
a) stabilization of rifaximin against degradation (e.g. hydrolysis, oxidation, etc)
b) water solubility
c) dissolution
d) free flowability and non-hygroscopicity
e) solubility, delivery and/or performance
f) safe handling According to yet another aspect of the present invention, there is provided a rifaximin complex as described above for use in medicine.

According to yet another aspect of the present invention, there is provided a rifaximin complex as described above for use in treating bowel related disorders.

According to yet another aspect of the present invention, there is provided a rifaximin complex as described above for use in treating a bowel related disorder selected from the group consisting of irritable bowel syndrome, diarrhea, traveler's diarrhea, microbe associated diarrhea, Crohn's disease, chronic pancreatitis, pancreatic insufficiency and/or colitis.

According to yet another aspect of the present invention, there is provided a rifaximin complex as described above for use in the treatment of travelers' diarrhea caused by noninvasive strains of *Escherichia coli*. The present invention further provides a rifaximin complex as described above for use in treating bowel disease.

According to yet another aspect of the present invention, there is provided the use of a rifaximin complex as described above for use in the manufacture of a medicament for treating travelers' diarrhea caused by noninvasive strains of *Escherichia coli* as well as for treating bowel disease.

According to yet another aspect of the present invention, there is provided a method of treating hypertension or benign prostatic hyperplasia or for treating bowel disease, comprising administering to a patient in need thereof a therapeutically effective amount of rifaximin complex as described above.

BRIEF DESCRIPTION OF ACCOMPANYING DRAWINGS

FIG. 1—intrinsic dissolution profile of (1:2 w/w rifaximin:PVP) PVP complex of rifaximin of the present invention compared with that of a physical mixture of β-rifaximin and PVP (1:2 w/w rifaximin:PVP) by an HPLC-UV method.

Figure 2:
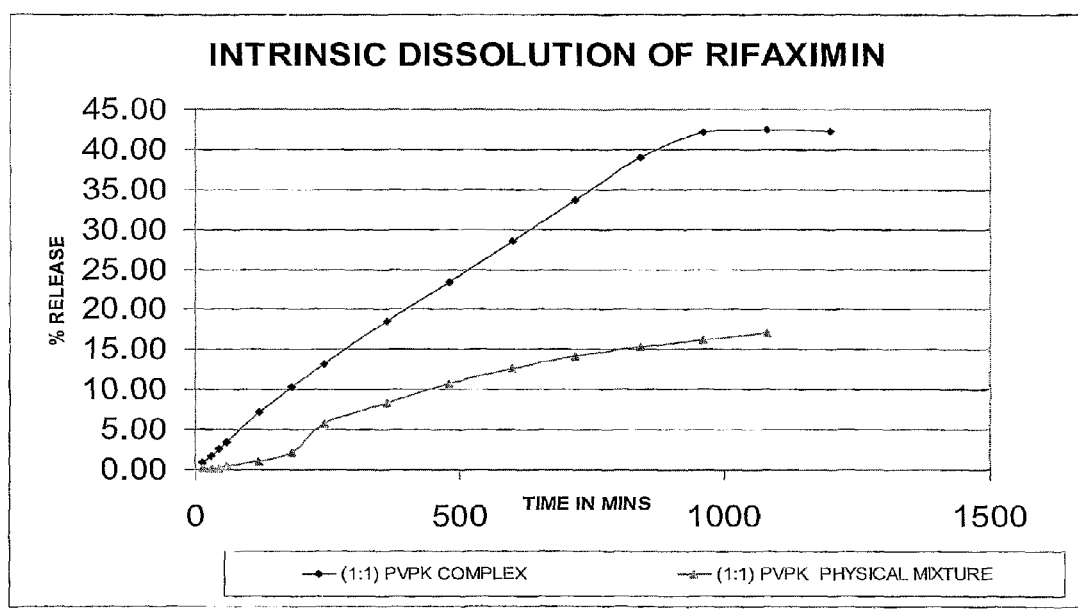
Figure 3:
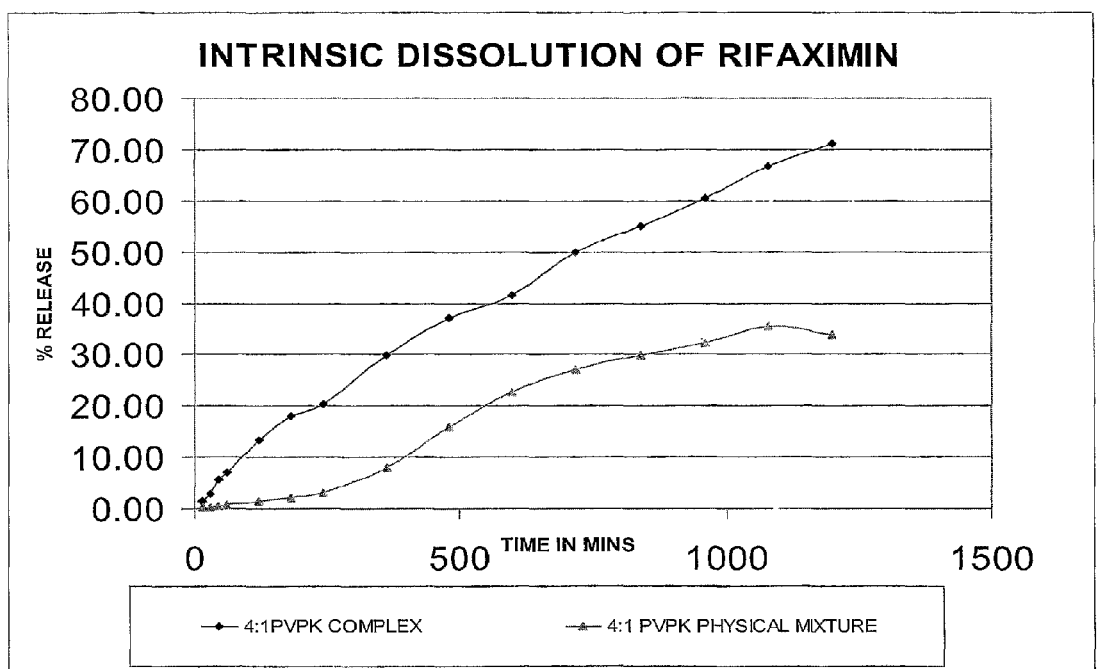

FIG. 2—intrinsic dissolution profile of (1:1 w/w rifaximin:PVP) PVP complex of rifaximin of the present invention compared with that of a physical mixture of β-rifaximin and PVP (1:1 w/w rifaximin:PVP) by an HPLC-UV method FIG. 3—intrinsic dissolution profile of (4:1 w/w rifaximin:PVP) PVP complex of rifaximin of the present invention compared with that of a physical mixture of β-rifaximin and PVP (4:1 w/w rifaximin:PVP) by an HPLC-UV method.

Figure 4:
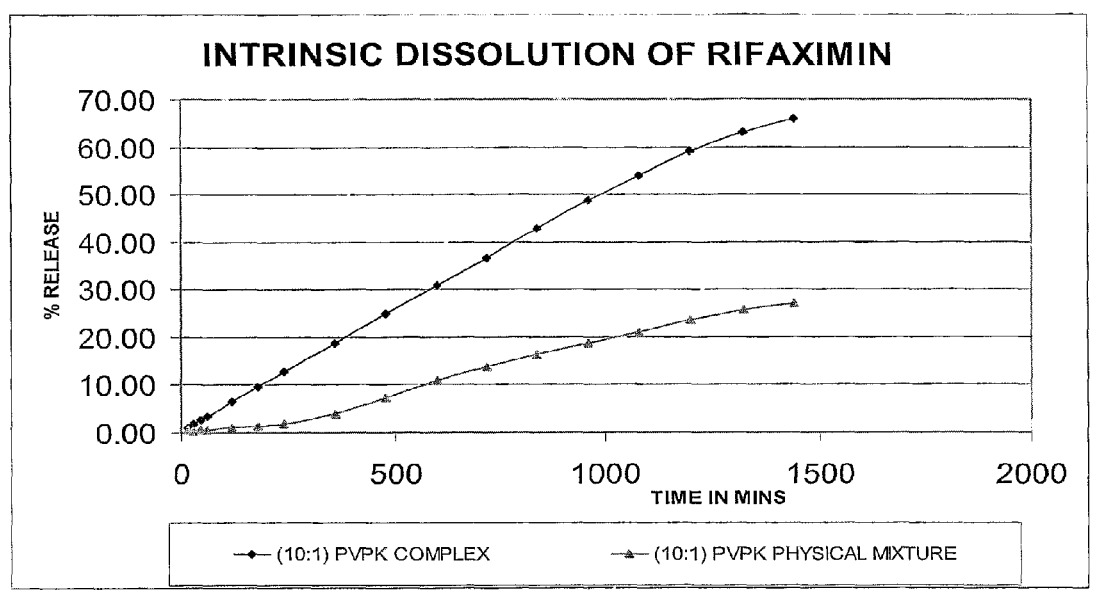

FIG. 4—intrinsic dissolution profile of (10:1 w/w rifaximin:PVP) PVP complex of rifaximin of the present invention compared with that of a physical mixture of β-rifaximin and PVP (10:1 w/w rifaximin:PVP) by an HPLC-UV method.

Figure 5:
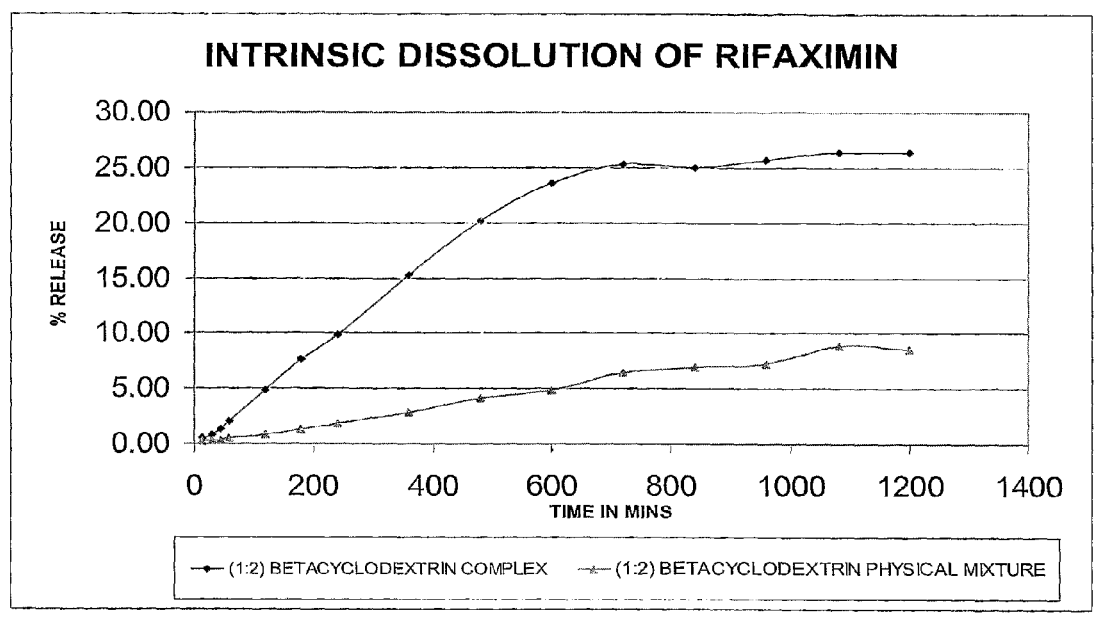

FIG. 5—intrinsic dissolution profile of (1:2 w/w rifaximin:β-CD) β-cyclodextrin complex of rifaximin of the present invention compared with that of a physical mixture of β-rifaximin and CD (1:2 w/w rifaximin:β-CD) by an HPLC-UV method.

Figure 6:
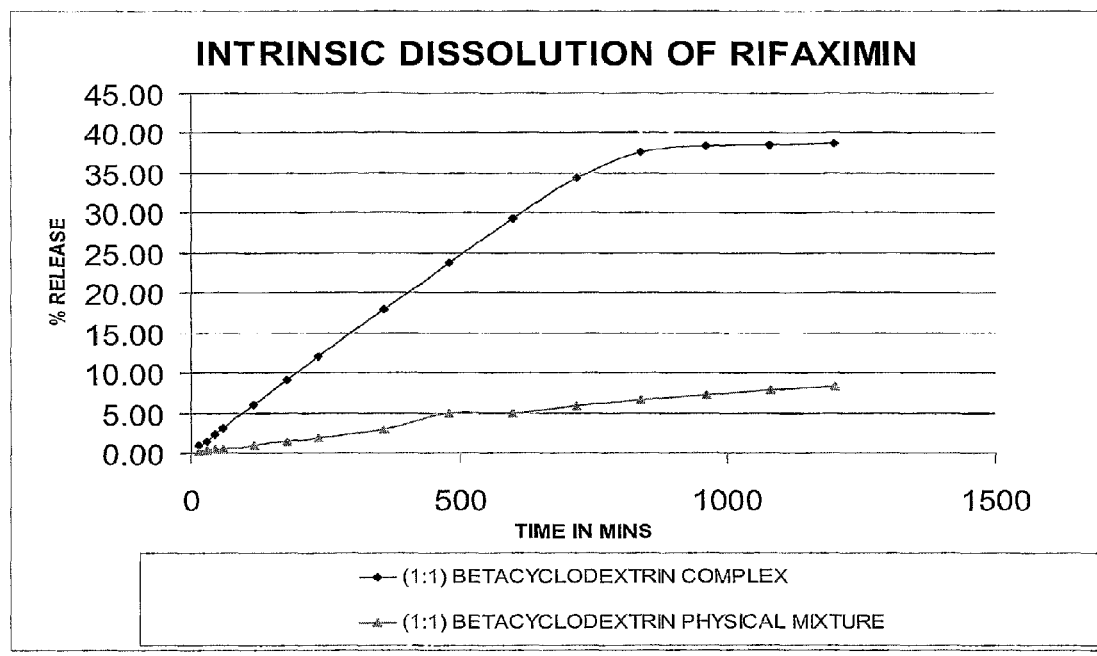
Figure 7:
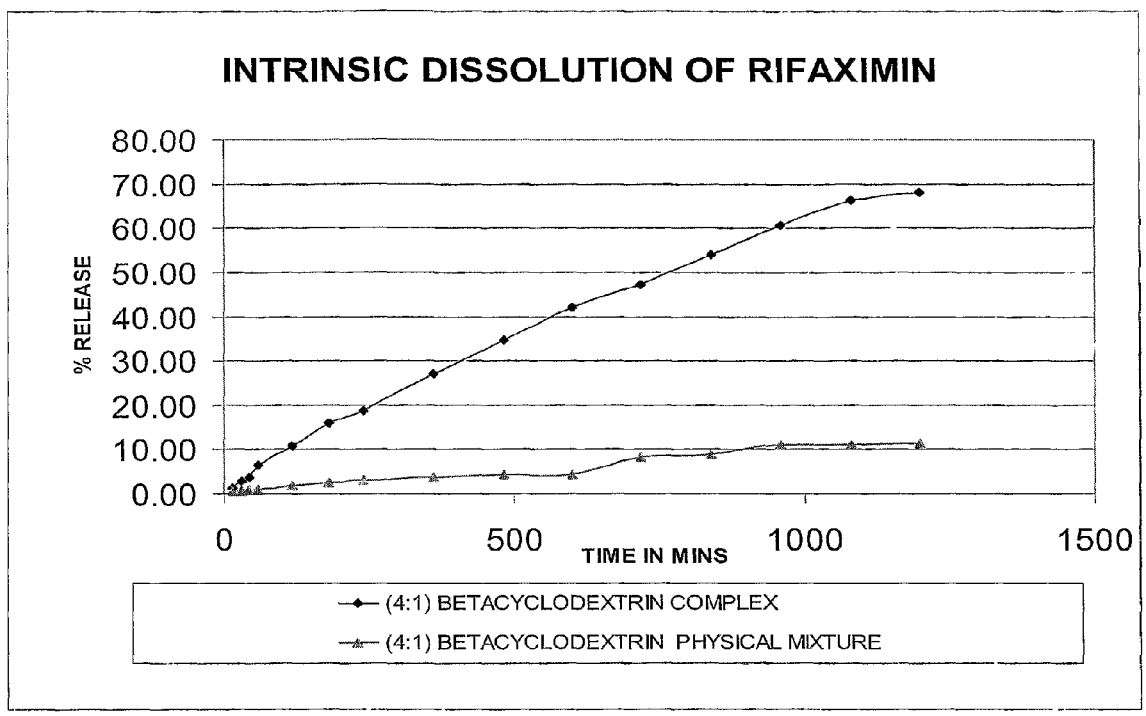

FIG. 6 indicates intrinsic dissolution profile of (1:1 w/w rifaximin:β-CD) β-cyclodextrin complex of rifaximin of the present invention compared with that of a physical mixture of β-rifaximin and CD (1:1 w/w rifaximin:β-CD) by an HPLC-UV method FIG. 7 indicates intrinsic dissolution profile of (4:1 w/w rifaximin:β-CD) β-cyclodextrin complex of rifaximin of the present invention compared with that of a physical mixture of β-rifaximin and CD (4:1 w/w rifaximin:β-CD) by an HPLC-UV method.

Figure 8:
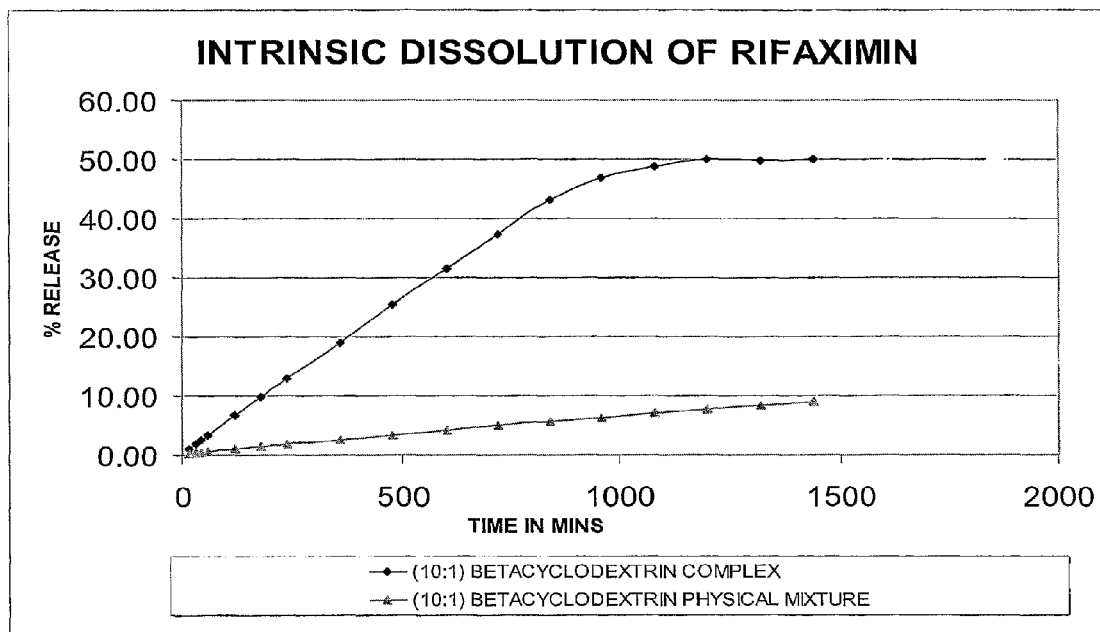

FIG. 8 indicates intrinsic dissolution profile of (10:1 w/w rifaximin:β-CD) β-cyclodextrin complex of rifaximin of the present invention compared with that of a physical mixture of β-rifaximin and CD (10:1 w/w rifaximin:β-CD) by an HPLC-UV method.

Figure 9:
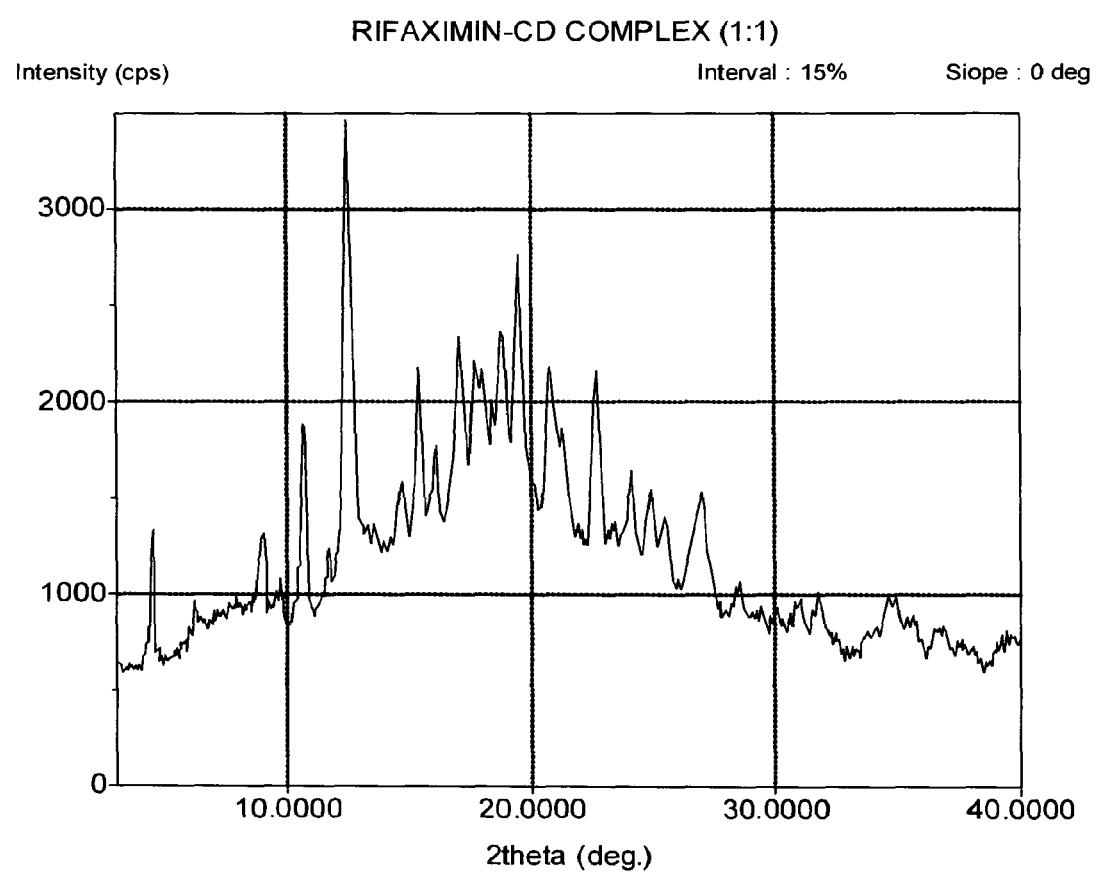

FIG. 9 indicates an X-ray powder diffractogram (XRD) of a β-cyclodextrin complex of rifaximin at 1:1 w/w concentration.

Figure 10:
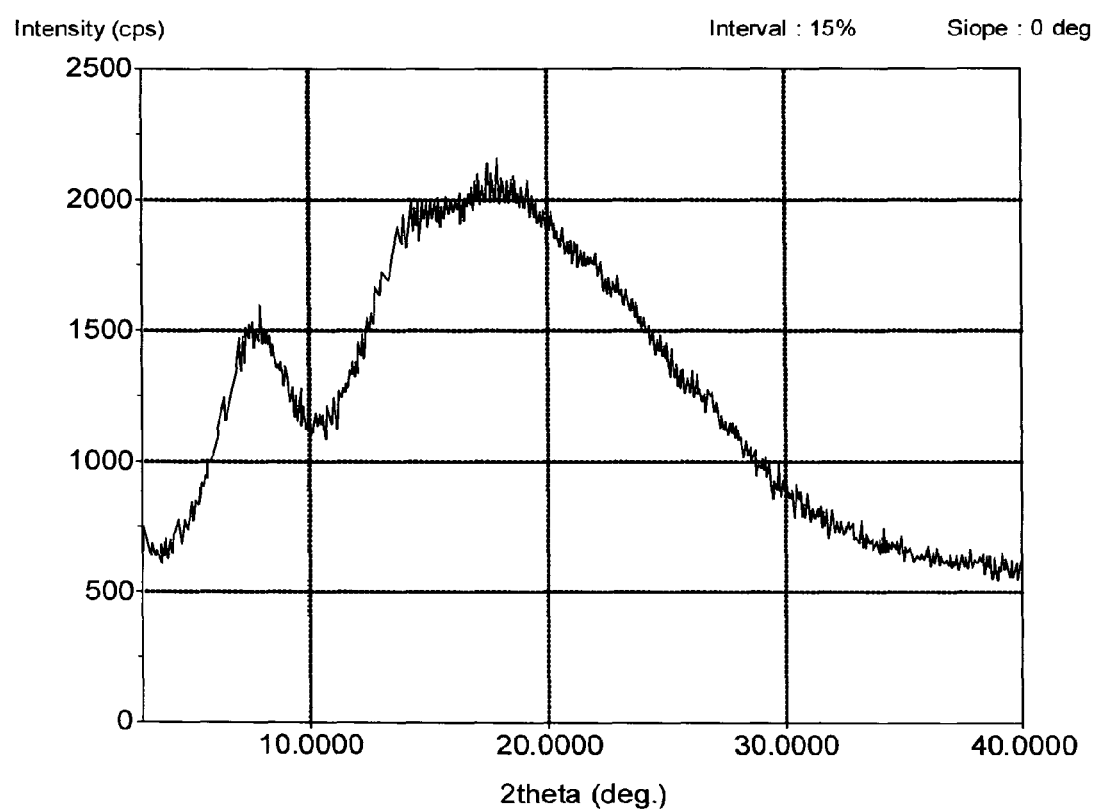

FIG. 10 indicates an X-ray powder diffractogram (XRD) of (10:1 w/w rifaximin:PVP) a PVP complex of rifaximin.

DETAILED DESCRIPTION OF THE INVENTION

The invention will now be described in detail in connection with certain preferred and optional embodiments, so that various aspects thereof may be more fully understood and appreciated.

The present invention provides a form of rifaximin with enhanced solubility and stability. This form of rifaximin comprises a complex of rifaximin with a complexing agent. The complexing agents used in the present invention include more particularly a polyvinyl pyrrolidone or a cyclodextrin.

There is also provided by the present invention a process for preparing the rifaximin-complexing agent complex of the present invention, the process comprising:
a) dissolving the rifaximin in a suitable solvent;
b) adding the complexing agent to the rifaximin solution either as such or in the form of solution to form a mixture;
c) isolating the complex, for example by concentrating the reaction mass obtained in step
b) and further drying to obtain the complex.

The rifaximin used in the process of the present invention may be obtained by any one of the methods disclosed in the prior art. For example, the rifaximin used in the process of the present invention may be in the polymorphic form α, β, γ, δ or ε. In a preferred embodiment of the present invention, the rifaximin used is in the β-form. The β-form of rifaximin is the least soluble known form of rifaximin.

The solvent used may be selected from ethers, alcohols, esters, aldehydes, halogenated solvents, hydrocarbons and combinations thereof.

In the process of the present invention, the complexing agent used may be selected from polyvinyl pyrrolidone (PVP) or cyclodextrin (CD).

Polyvinyl pyrrolidone (PVP, also known as "povidone") is commercially available as a white powder of a given molecular weight. Generally, the molecular weights of PVP polymers are given by their K-values, e.g., K-15 to K-90. The K-value indicates the average molecular weight ranging from 20,000 to 1,000,000. A preferred PVP is K-30, typically having a molecular weight of about 40,000. An unusual property of PVP is its solubility in water as well as in various organic solvents.

In the process of the present invention, the PVP may be selected from the group consisting of PVP K-12, K-15, K-17, K-25, K-30, K-60, K-80, K-90 and K-120. Preferably, K-25, K-30, K-90, and most preferably K-30.

In the process of the present invention, the cyclodextrin used to form the complex may be in any form of cyclodextrin, including α-cyclodextrin having 6 glucose units, β-cyclodextrin having 7 glucose units, or γ-cyclodextrin having 8 glucose units. The cyclodextrin may also be in anhydrous or hydrated form. The preferred cyclodextrin is β-cyclodextrin.

The complexing agent may be added as such or as a solution in a suitable solvent. The amount of rifaximin that can be encapsulated is directly related to the molecular weight of the rifaximin.

In some embodiments, one mole of complexing agent encapsulates one mole of rifaximin. Preferably, the amounts of rifaximin and complexing agent used in the formulation are typically sufficient to provide the desired therapeutic effect. On a weight basis, the ratio between rifaximin and complexing agent in the given composition (termed "w/w"), ranges from 20:1 to 1:20, preferably from 10:1 to 1:2. Typically, the ratio of rifaximin to complexing agent ranges from 4:1 to 1:2. The ratio may be 1:1.

The solvent may be removed rapidly and completely by vacuum drying or vacuum evaporation. In an embodiment, the solvent may be removed by spray drying to yield the rifaximin complex. In another embodiment, the rifaximin complex may be obtained freeze drying. In yet another embodiment, the rifaximin complex may be isolated by microwave treatment techniques.

According to a third aspect of the present invention, there is provided a rifaximin complex which enhances at least one of the following:
a) stabilization of rifaximin against degradation (e.g. hydrolysis, oxidation, etc)
b) enhancement of water solubility of rifaximin
c) better dissolution
d) free flowing and non-hygroscopic rifaximin
e) modified solubility, delivery or performance
f) safe handling of rifaximin The rifaximin complex of the present invention is not a simple physical mixture of the ingredients. This rifaximin complex is superior to the conventional free base of rifaximin, for example in terms of storage stability.

Further, it was observed that the use of a complexing agent as an excipient in the formulation enhances solubility to some extent but the formation of a complex with rifaximin enhances solubility much more than mixing it physically as an excipient. Further, the aqueous solubility of the rifaximin complex with cyclodextrin or PVP is found to be greater than the aqueous solubility of rifaximin. The enhanced solubility of the complex can further increase dissolution rate as shown in FIGS. 1 to 8 and thus makes these complexes more bio-available in the body. This increase in bioavailability and stability of the complex further allows for smaller doses to achieve the desired therapeutic effect compared to a larger dose of rifaximin alone. Further, these complexes avoid interconversion of crystalline forms of rifaximin. In addition, these complexes can be used to reduce or prevent gastrointestinal and ocular irritation, to reduce or eliminate unpleasant smells or tastes, as well as to prevent drug-drug or drug-additive interactions.

According to another aspect of the present invention, there is provided a rifaximin complex characterized by having an intrinsic dissolution profile as shown in any one of FIGS. 1 to 8.

To measure the intrinsic dissolution of a rifaximin complex, for example a rifaximin-PVP complex or a rifaximin-CD complex, rifaximin samples were measured to compare the influence of the different parameter settings. At appropriate time intervals, an automated sample collector removes aliquots from the dissolution medium for analysis. The time interval for sampling can vary, for example, from 2 to 30 minutes, depending on the properties of the drug and dissolution medium used. Suitable dissolution equipment for these operations includes LAB INDIA DISSO 2000.

The complexes may be used in a variety of applications. In an embodiment, the composition of the present invention is in the form of a tablet, a capsule or a liquid oral. The composition may further optionally include additional components to enhance or achieve the desired therapeutic effect of rifaximin. Examples of such components include, but are not limited to surfactants, excipients, disintegrating agents, binders, lubricants, dispersing agents, thickening agents.

The present invention will now be further illustrated by the following examples, which do not limit the scope of the invention in any way.

Example 1—Preparation of Rifaximin-PVP Complex (1:2 w/w Ratio)

Preparation 1

2 g of rifaximin was dissolved in 30 ml of ethanol at 25-30° C. 4 g of PVP K-30 was dissolved in 40 ml ethanol. The solution of PVP K-30 was added to the rifaximin solution and stirred. The reaction mass was concentrated under vacuum at 35° C. till dryness and then dried completely at 30-35° C. for 24 hours to get 5.4 g rifaximin-PVP complex.

Preparation 2

5 g of rifaximin was dissolved in 75 ml of ethanol at 25-30° C. The reaction mass was heated to 35° C. and 10 g of PVP K-30 was added to the rifaximin solution and stirred. The reaction mass was concentrated under vacuum at 35° C. till dryness and then dried completely at 30-35° C. for 24 hours to get 13 g rifaximin-PVP complex.

Example 2—Preparation of Rifaximin-PVP Complex (1:1 w/w Ratio)

Preparation 1

2 g of rifaximin was dissolved in 30 ml of ethanol at 25-30° C. 2 g of PVP K-30 was dissolved in 20 ml of ethanol. The solution of PVP K-30 was added to the rifaximin solution and stirred. The reaction mass was concentrated under vacuum at 35° C. till dryness and then dried completely at 30-35° C. for 24 hours to get 3.1 g rifaximin-PVP complex.

Preparation 2

5 g of rifaximin was dissolved in 75 ml of ethanol at 25-30° C. The reaction mass was heated to 35° C. and 5 g of PVP K-30 was added to the rifaximin solution and stirred. The reaction mass was concentrated under vacuum at 35° C. till dryness and then dried completely at 30-35° C. for 24 hours to get 8.8 g rifaximin-PVP complex.

Example 3—Preparation of Rifaximin-PVP Complex (4:1 w/w Ratio)

Preparation 1

10 g of rifaximin was dissolved in 150 ml of ethanol at 30-35° C. A solution of PVP K-30 was prepared by dissolving 2.5 g of PVP K-30 in 25 ml of ethanol. This solution was added to the rifaximin solution at 30-35° C. The reaction mass was stirred, concentrated to dryness under vacuum at 30-35° C. and then dried completely at 70° C. for 24-30 hours to get 12.5 g rifaximin-PVP complex.

Preparation 2

5 g of rifaximin was dissolved in 75 ml of ethanol at 25-30° C. The reaction mass was heated to 35° C. and 1.25 g of PVP K-30 was added to the rifaximin solution and stirred. The reaction mass was concentrated under vacuum at 35° C. till dryness and then dried completely at 30-35° C. for 24 hours to get 5.5 g rifaximin-PVP complex.

Example 4—Preparation of Rifaximin-PVP Complex (10:1 w/w Ratio)

Preparation 1

10 g of rifaximin was dissolved in 150 ml of ethanol at 30-35° C. A solution of PVP K-30 was prepared by dissolving 1 g of PVP K-30 in 15 ml of ethanol. The solution was added to the rifaximin solution. The reaction mass was stirred at 30-35° C., concentrated to dryness under vacuum at 30-35° C. and then dried completely at 30-35° C. for 24-30 hours to get 10.3 g rifaximin-PVP complex.

Preparation 2

5 g of rifaximin was dissolved in 75 ml of ethanol at 25-30° C. The reaction mass was heated to 35° C. and 0.5 g of PVP K-30 was added to the rifaximin solution and stirred. The reaction mass was concentrated under vacuum at 35° C. till dryness and then dried completely at 30-35° C. for 24 hours to get 5.0 g rifaximin-PVP complex.

Example 5—Preparation of the Rifaximin-β-Cyclodextrin Complex (1:2 w/w Ratio)

Preparation 1

2 g of rifaximin was dissolved in 30 ml of ethanol at 25-30° C. To this solution 4 g of β-cyclodextrin was added and stirred. The reaction mass was concentrated under vacuum at 35° C., stripped with 20 ml of ethanol. This residue was concentrated to dryness and dried under vacuum at 30-35° C. for 20-24 hours to get 5.1 g rifaximin-β cyclodextrin complex.

Preparation 2

4 g of rifaximin was dissolved in 60 ml of ethanol at 25-30° C. The reaction mass was heated to 35° C. and 8 g of β-cyclodextrin was added to the rifaximin solution and stirred. The reaction mass was concentrated under vacuum at 35° C. till dryness and then dried completely at 30-35° C. for 24 hours to get 10.7 g rifaximin-β cyclodextrin complex.

Example 6—Preparation of Rifaximin β-Cyclodextrin Complex (1:1 w/w Ratio)

2 g of rifaximin was dissolved in 30 ml of ethanol at 25-30° C. To this solution 2 g of β-cyclodextrin was added and stirred. The reaction mass was concentrated under vacuum at 35° C. and then dried completely at 30-35° C. for 20-24 hours to get 2.8 g rifaximin-β cyclodextrin complex.

Example 7—Preparation of the Rifaximin-6-Cyclodextrin Complex (4:1 w/w Ratio)

7 g of rifaximin was dissolved in 100 ml of ethanol at 30-35° C. To this solution 1.75 g of β-cyclodextrin was added and stirred. The reaction mass was stirred, concentrated to dryness under vacuum at 30-35° C. and then dried completely at 30-35° C. for 24-30 hours to get 8.1 g rifaximin-β cyclodextrin complex.

Example 8—Preparation of the Rifaximin-β-Cyclodextrin Complex (10:1 w/w Ratio)

7 g of rifaximin was dissolved in 100 ml of ethanol at 30-35° C. To this solution 0.7 g of β-cyclodextrin was added and stirred. The reaction mass was stirred, concentrated to dryness under vacuum at 30-35° C. and then dried completely at 30-35° C. for 24-30 hours to get 6.75 g rifaximin-β cyclodextrin complex.

Comparative Intrinsic Dissolution Study

Example 9—Preparation of Tablet

General Process for Preparing Tableting Mixture Comprising Rifaximin Complex:

A tableting mixture (100 mg) comprising solely rifaximin complex prepared according to any of the examples 1 to 8 (i.e. with no excipients) was prepared and compressed to a pellet using a manual hand press operating at a compression pressure of 2.5 tones for 5 minutes.

General Process for Preparing Tableting Mixture Comprising a Physical Mixture of Rifaximin and Complexing Agent:

Similarly a tableting mixture (100 mg) comprising a solely physical mixture of rifaximin and complexing agent in the proportionate ratio (i.e. with no excipients) was prepared by mixing the rifaximin and complexing agent in the desired ratio in a mortar and pestle for 5 minutes and compressing to a pellet using a manual hand press operating at a compression pressure of 2.5 tones for 5 minutes.

Example 10—Preparation of 1:2 Physical Mixture Comprising Rifaximin and PVPK (where PVPK is PVP K-30)

100 mg of input API of rifaximin and 200 mg of PVPK were mixed uniformly and used for pellet preparation. (Inj volume: 30 μl)

In-vitro dissolution studies were performed on the 100 mg pellet in a LAB INDIA DISSO 2000.

The pellet was fixed in a PFTE holder, such that only the pellet surface came into contact with the dissolution medium. The PFTE loaded holder was placed in the dissolution vessel containing 900 ml of 0.1M of sodium dihydrogen phosphate having pH 7.4 at 37±0.5° C. Two pellets were measured for each run of the design of the experiments. Stirring was performed with a paddle rotating at 100 rpm. The dissolution was followed up to 1440 min and the concentration of active ingredient, rifaximin, dissolved in the test medium was determined by removing samples of 10 ml at the specified time.

The concentration of rifaximin complex was quantified by HPLC UV method at a maximum wavelength of 300 nm under the conditions as specified below:

| | |
|---|---|
| Mobile Phase | Buffer:Acetonitrile: 45:55 |
| Buffer | 0.025M Sodium dihydrogen phosphate. The pH adjusted to 3.0 with orthophosphoric acid |
| Column | Zorbax SB-phenyl, 4.6 mm, 5 μm |
| Column Temp | 25° C. |
| Flow | 1.0 ml/min |
| Injection Volume | 30 μL |
| Diluent | Buffer:Acetonitrile: 1:1 |
| Standard Preparation | 25 mg standard dissolved to 25 ml with diluent. 5 ml of this solution diluted to 50 ml with dissolution medium. |

The percentage of rifaximin released from the PVPK complex (1:2 w/w) as well as from the physical mixture (1:2 w/w) were plotted against time as shown in FIG. 1. The intrinsic dissolution rate was derived from the slope of this curve. Table 1 shows the results in tabular form.

TABLE 1

| TIME IN MINS | (1:2) PVP COMPLEX | (1:2) PVPK PHYSICAL MIXTURE |
|---|---|---|
| 15 | 0.65 | 0.12 |
| 30 | 0.97 | 0.11 |
| 45 | 1.92 | 0.14 |
| 60 | 2.62 | 0.19 |
| 120 | 6.42 | 0.42 |
| 180 | 9.78 | 1.34 |
| 240 | 11.51 | 3.10 |
| 360 | 15.98 | 10.09 |
| 480 | 20.08 | 15.48 |
| 600 | 26.79 | 18.02 |
| 720 | 30.40 | 21.20 |
| 840 | 31.25 | 21.10 |
| 960 | 32.40 | 22.78 |
| 1080 | 31.40 | 23.65 |
| 1200 | 30.86 | 22.66 |

Example 11—Preparation of 1:1 Physical Mixture Comprising Rifaximin and PVPK 100 mg of input API of rifaximin and 100 mg PVPK respectively were mixed uniformly and used for pellet preparation. (Inj volume: 20 μl)

The percentage of rifaximin released from the PVP complex (1:1 w/w) as well as from the physical mixture (1:1 w/w) were plotted against time as shown in FIG. 2. The intrinsic dissolution rate was derived from the slope of this curve. Table 2 shows the results in tabular form.

TABLE 2

| TIME IN MINS | (1:1) PVP COMPLEX | (1:1) PVP PHYSICAL MIXTURE |
|---|---|---|
| 15 | 0.86 | 0.19 |
| 30 | 1.71 | 0.16 |
| 45 | 2.54 | 0.19 |
| 60 | 3.39 | 0.20 |
| 120 | 7.15 | 0.37 |
| 180 | 10.39 | 0.94 |
| 240 | 13.21 | 2.22 |
| 360 | 18.45 | 5.69 |
| 480 | 23.42 | 8.33 |
| 600 | 28.48 | 10.72 |
| 720 | 33.64 | 12.67 |

TABLE 2-continued

| TIME IN MINS | (1:1) PVP COMPLEX | (1:1) PVP PHYSICAL MIXTURE |
|---|---|---|
| 840 | 38.94 | 14.23 |
| 960 | 42.13 | 15.28 |
| 1080 | 42.46 | 16.17 |
| 1200 | 42.26 | 16.99 |

Example 12—Preparation of 4:1 Physical Mixture Comprising Rifaximin and PVPK 100 mg of input API of rifaximin and 25 mg PVPK were mixed uniformly and used for pellet preparation. (Inj volume: 15 μl)

The percentage of rifaximin released from the PVP complex (4:1 w/w) as well as from the physical mixture (4:1 w/w) were plotted against time as shown in FIG. 3. The intrinsic dissolution rate was derived from the slope of this curve. Table 3 shows the results in tabular form.

TABLE 3

| TIME IN MINS | (4:1) PVPK COMPLEX | (4:1) PVPK PHYSICAL MIXTURE |
|---|---|---|
| 15 | 1.37 | 0.17 |
| 30 | 2.68 | 0.27 |
| 45 | 5.65 | 0.48 |
| 60 | 7.09 | 0.77 |
| 120 | 13.22 | 1.29 |
| 180 | 18.01 | 2.06 |
| 240 | 20.34 | 3.09 |
| 360 | 29.76 | 7.99 |
| 480 | 37.20 | 15.86 |
| 600 | 41.53 | 22.53 |
| 720 | 49.81 | 27.01 |
| 840 | 54.99 | 29.87 |
| 960 | 60.41 | 32.22 |
| 1080 | 66.82 | 35.53 |
| 1200 | 71.08 | 33.83 |

Example 13—Preparation of 10:1 Physical Mixture Comprising Rifaximin and PVPK 100 mg of input API of rifaximin and 10 mg PVPK were mixed uniformly and used for pellet preparation. (Inj volume: 10 μl)

The percentage of rifaximin released from the PVP complex (10:1 w/w) as well as from the physical mixture (10:1 w/w) were plotted against time as shown in FIG. 4. The intrinsic dissolution rate was derived from the slope of this curve. Table 4 shows the results in tabular form.

TABLE 4

| TIME IN MINS | (10:1) PVPK COMPLEX | (10:1) PVPK PHYSICAL MIXTURE |
|---|---|---|
| 15 | 1.01 | 0.41 |
| 30 | 1.81 | 0.38 |
| 45 | 2.63 | 0.44 |
| 60 | 3.41 | 0.54 |
| 120 | 6.50 | 0.94 |
| 180 | 9.65 | 1.34 |
| 240 | 12.76 | 1.83 |
| 360 | 18.78 | 3.86 |
| 480 | 24.96 | 7.32 |
| 600 | 30.90 | 10.83 |
| 720 | 36.68 | 13.82 |
| 840 | 42.74 | 16.43 |
| 960 | 48.70 | 18.73 |
| 1080 | 53.95 | 21.13 |
| 1200 | 59.02 | 23.50 |
| 1320 | 63.10 | 25.54 |
| 1440 | 65.72 | 27.08 |

Example 14

Example 10 was repeated using Beta cyclodextrin instead of PVPK and the percentage of rifaximin released from the CD complex (1:2 w/w) as well as from the physical mixture (1:2 w/w) were plotted against time as shown in FIG. 5. The intrinsic dissolution rate was derived from the slope of this curve. Table 5 shows the results in tabular form.

TABLE 5

| TIME IN MINS | (1:2) BETA CYCLODEXTRIN COMPLEX | (1:2) BETA CYCLODEXTRIN PHYSICAL MIXTURE |
|---|---|---|
| 15 | 0.48 | 0.17 |
| 30 | 0.82 | 0.25 |
| 45 | 1.35 | 0.35 |
| 60 | 2.05 | 0.48 |
| 120 | 4.83 | 0.80 |
| 180 | 7.67 | 1.33 |
| 240 | 9.87 | 1.81 |
| 360 | 15.23 | 2.82 |
| 480 | 20.21 | 4.14 |
| 600 | 23.58 | 4.84 |
| 720 | 25.33 | 6.43 |
| 840 | 24.97 | 6.97 |
| 960 | 25.67 | 7.19 |
| 1080 | 26.37 | 8.80 |
| 1200 | 26.37 | 8.50 |

Example 15

Example 11 was repeated using Beta cyclodextrin instead of PVPK and the percentage of rifaximin released from the CD complex (1:1 w/w) as well as from the physical mixture (1:1 w/w) were plotted against time as shown in FIG. 6. The intrinsic dissolution rate was derived from the slope of this curve. Table 6 shows the results in tabular form.

TABLE 6

| TIME IN MINS | (1:1) BETA CYCLODEXTRIN COMPLEX | (1:1) BETA CYCLODEXTRIN PHYSICAL MIXTURE |
|---|---|---|
| 15 | 0.85 | 0.17 |
| 30 | 1.46 | 0.29 |
| 45 | 2.29 | 0.40 |
| 60 | 3.04 | 0.53 |
| 120 | 6.02 | 0.95 |
| 180 | 9.07 | 1.39 |
| 240 | 12.08 | 1.89 |
| 360 | 17.88 | 2.86 |
| 480 | 23.66 | 4.97 |
| 600 | 29.22 | 4.93 |
| 720 | 34.43 | 5.88 |
| 840 | 37.54 | 6.69 |
| 960 | 38.32 | 7.27 |
| 1080 | 38.49 | 7.82 |
| 1200 | 38.66 | 8.32 |

Example 16

Example 12 was repeated using Beta cyclodextrin instead of PVPK and the percentage of rifaximin released from the CD complex (4:1 w/w) as well as from the physical mixture (4:1 w/w) were plotted against time as shown in FIG. 7. The intrinsic dissolution rate was derived from the slope of this curve. Table 7 shows the results in tabular form.

TABLE 7

| TIME IN MINS | (4:1)BETA CYCLODEXTRIN | (4:1) BETA CYCLODEXTRIN PHYSICAL MIXTURE |
|---|---|---|
| 15 | 1.09 | 0.52 |
| 30 | 2.85 | 0.64 |
| 45 | 3.54 | 0.81 |
| 60 | 6.29 | 1.01 |
| 120 | 10.61 | 1.91 |
| 180 | 15.88 | 2.33 |
| 240 | 18.66 | 3.09 |
| 360 | 26.97 | 3.64 |
| 480 | 34.74 | 4.28 |
| 600 | 42.07 | 4.36 |
| 720 | 47.29 | 8.14 |
| 840 | 54.05 | 8.92 |
| 960 | 60.82 | 11.09 |
| 1080 | 66.13 | 10.90 |
| 1200 | 68.04 | 11.39 |

Example 17

Example 13 was repeated using Beta cyclodextrin instead of PVPK and the percentage of rifaximin released from the CD complex (10:1 w/w) as well as from the physical mixture (10:1 w/w) were plotted against time as shown in FIG. 8. The intrinsic dissolution rate was derived from the slope of this curve. Table 8 shows the results in tabular form.

TABLE 8

| TIME IN MINS | (10:1) BETA CYCLODEXTRIN | (10:1) BETA CYCLODEXTRIN PHYSICAL MIXTURE |
|---|---|---|
| 15 | 0.96 | 0.28 |
| 30 | 1.78 | 0.38 |
| 45 | 2.58 | 0.49 |
| 60 | 3.36 | 0.56 |
| 120 | 6.65 | 1.00 |
| 180 | 9.84 | 1.37 |
| 240 | 12.87 | 1.78 |
| 360 | 19.00 | 2.58 |
| 480 | 25.52 | 3.41 |
| 600 | 31.48 | 4.22 |
| 720 | 37.35 | 4.92 |
| 840 | 43.19 | 5.65 |
| 960 | 46.88 | 6.34 |
| 1080 | 48.74 | 7.01 |
| 1200 | 49.97 | 7.67 |
| 1320 | 49.81 | 8.28 |
| 1440 | 50.01 | 8.86 |

The results were reported on an average of 2 results each.

When compared with a physical mixture of rifaximin with a complexing agent, the rifaximin complex exhibited a superior rate of dissolution as shown in Tables 9 and 10 below.

The percentage of actual release of rifaximin is calculated from the characteristics data obtained in the FIGS. 1 to 8. The formula for calculating the percentage of actual release of rifaximin from the complex is given below:

$$\% \text{ of actual release of rifaximin} = \frac{\% \text{ relese of rifaximin from the complex}}{\text{wt \% of rifaximin in the complex}} \times 100$$

TABLE 9

The Actual release of Rifaximin from Rifaximin-PVP complex compared with physical mixture:-

| Content of complexing agent (w/w) | % Rifaximin released from PVP complex | % Rifaximin released from Physical mixture |
|---|---|---|
| 1:2 | 92.67 | 68.05 |
| 1:1 | 84.52 | 33.98 |
| 4:1 | 88.85 | 42.29 |
| 10:1 | 73.00 | 30.09 |

The above data shows that the PVP complex has more advantage over a physical mixture. This advantage is maximum at lower concentration of PVP i.e. when ratio is 10:1 (73:30), whereas at high concentration i.e. when ratio is 1:2 or 33.3% the advantage is about 1.36 times (92.67:68.05)

TABLE 10

The Actual release of Rifaximin from Rifaximin-CD complex compared with physical mixture:-

| Content of complexing agent (w/w) | % Rifaximin released from CD complex | % Rifaximin released from Physical mixture |
|---|---|---|
| 1:2 | 79.18 | 25.52 |
| 1:1 | 77.32 | 16.64 |
| 4:1 | 85.00 | 14.23 |
| 10:1 | 55.55 | 9.84 |

The above data shows that, the CD complex has more advantage over a physical mixture. This advantage is maximum at a lower concentration of CD i.e. when the ratio is 10:1 (55.55:9.84), whereas at high concentration i.e. when ratio is 1:2 or 33.3% the advantage is about 3.1 times (79.18: 25.52)

These results further proved that rifaximin complex had been formed after this technique.

It will be appreciated that the invention may be modified within the scope of the appended claims.

The invention claimed is:

1. A process for preparing a complex of rifaximin and a complexing agent comprising a) dissolving rifaximin in a solvent; b) adding the complexing agent to the solution of rifaximin; and c) isolating the rifaximin complex from the solution,
   wherein the complex is in an amorphous form and exhibits enhanced solubility compared to a physical mixture of rifaximin and the complexing agent.

2. A process according to claim 1, wherein the solvent is selected from the group consisting of an ether, an alcohol, an ester, an aldehyde, a halogenated solvent, a hydrocarbon and mixtures thereof.

3. A process according to claim 2, wherein the complexing agent is added to the rifaximin solution in the form of a solution with a solvent, and the complexing agent solvent is selected from the group consisting of an ether, an alcohol, an ester, an aldehyde, a halogenated solvent, a hydrocarbon and mixtures thereof.

4. A process according to claim 3, wherein the solvent for the rifaximin and/or the solvent for the complexing agent comprises ethanol.

5. A process according to claim 1, wherein the isolation comprises concentrating the reaction mass and drying to obtain the isolated complex.

6. A process according to claim 1, wherein the complexing agent comprises polyvinyl pyrrolidone (PVP) or a cyclodextrin (CD).

7. A process according to claim 6, wherein the complexing agent is a PVP having a K-value ranging from K-15 to K-90.

8. A process according to claim 6, wherein the complexing agent is a PVP selected from the group consisting of PVP K-12, K-15, K-17, K-25, K-30, K-60, K-80, K-90 and K-120.

9. A process according to claim 8, wherein the complexing agent is PVP K-30.

10. A process according to claim 6, wherein the complexing agent comprises an unmodified cyclodextrin.

11. A process according to claim 6, wherein the complexing agent is a cyclodextrin selected from the group consisting of α-cyclodextrin, β-cyclodextrin and γ-cyclodextrin.

12. A process according to claim 11, wherein the cyclodextrin is β-cyclodextrin.

13. A process according to claim 1, wherein the ratio of rifaximin to complexing agent in the complex ranges from 20:1 w/w to 1:20 w/w.

14. A process according to claim 1, wherein the ratio of rifaximin to complexing agent in the complex ranges from 10:1 w/w to 1:2 w/w.

15. A process according to claim 1, wherein the ratio of rifaximin to complexing agent in the complex ranges from 4:1 w/w to 1:2 w/w.

16. A process according to claim 1, wherein the ratio of rifaximin to complexing agent in the complex is about 1:1.

17. A process according to claim 1, wherein the resulting complex is characterized by having an intrinsic dissolution profile as shown in any one of FIGS. 1 to 8.

18. A process according to claim 1, wherein the resulting complex is characterized by having an intrinsic dissolution profile that is substantially similar to any of FIGS. 1-8.

19. A process according to claim 1, wherein the resulting complex is characterized by the XRD pattern shown in FIG. 9.

20. A process according to claim 1, wherein the resulting complex is characterized by the XRD pattern shown in FIG. 10.

21. A process according to claim 1, wherein the resulting complex is characterized by an XRD pattern substantially similar to FIG. 9.

22. A process according to claim 1, wherein the resulting complex is characterized by an XRD pattern substantially similar to FIG. 10.

* * * * *